United States Patent [19]

McKee

[11] 4,321,916
[45] Mar. 30, 1982

[54] EYELID RETRACTOR

[76] Inventor: Douglas C. McKee, 66289 Riverside Rd., Montrose, Colo. 81401

[21] Appl. No.: 134,066

[22] Filed: Mar. 26, 1980

[51] Int. Cl.³ .............................................. A61B 17/02
[52] U.S. Cl. ...................................................... 128/20
[58] Field of Search ....................... 128/20, 17, 16, 11, 128/10

[56] References Cited

U.S. PATENT DOCUMENTS

| | | |
|---|---|---|
| 776,302 | 11/1904 | Crockett . |
| 2,438,646 | 3/1948 | Pulliam . |
| 2,845,925 | 5/1958 | Jayle . |
| 3,054,398 | 9/1962 | Kobler . |
| 3,313,294 | 4/1967 | Uddenberg . |
| 4,036,230 | 7/1977 | Adams . |
| 4,037,589 | 7/1977 | McReynolds .......................... 128/20 |
| 4,165,746 | 8/1979 | Burgin . |
| 4,177,802 | 12/1979 | Ogami . |

FOREIGN PATENT DOCUMENTS 114051   3/1918   United Kingdom .................. 128/20

OTHER PUBLICATIONS

Sklar Products Catalogue, pp. 223–224.
Wech Catalogue specula section.

Primary Examiner—Robert W. Michell
Assistant Examiner—Nancy A. B. Swisher
Attorney, Agent, or Firm—Fishburn, Gold and Litman

[57] ABSTRACT

An eyelid retractor is provided for maintaining the eyelids of a patient in an open position during ocular surgery or the like. The retractor comprises a loop having a smooth surface with eyelid restraining blades positioned on opposite sides thereof. The retractor is sufficiently malleable to be inelastically deformed such that the blades are in a desired eyelid retracting configuration and the retractor loop is also bent to conform to the face of the patient such that the retractor is supported by the face. The retractor is face hugging so as to exhibit a low profile. The retractor is also sufficiently resilient to oppose movement of the eyelids when in the eyelid retracting configuration.

15 Claims, 5 Drawing Figures

U.S. Patent Mar. 30, 1982 4,321,916
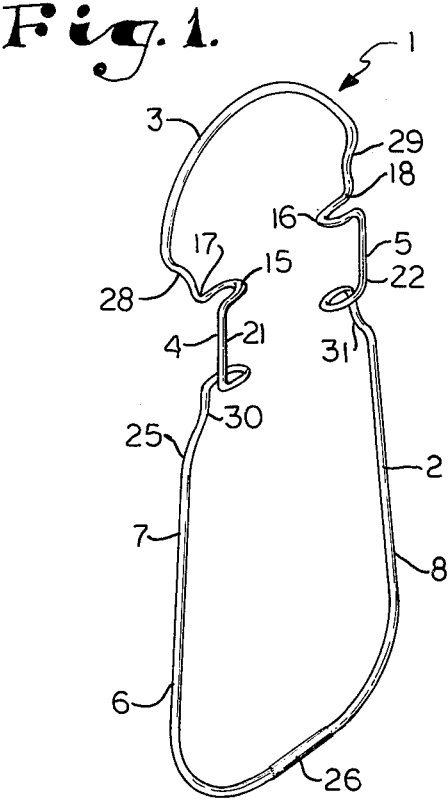
Fig. 1.
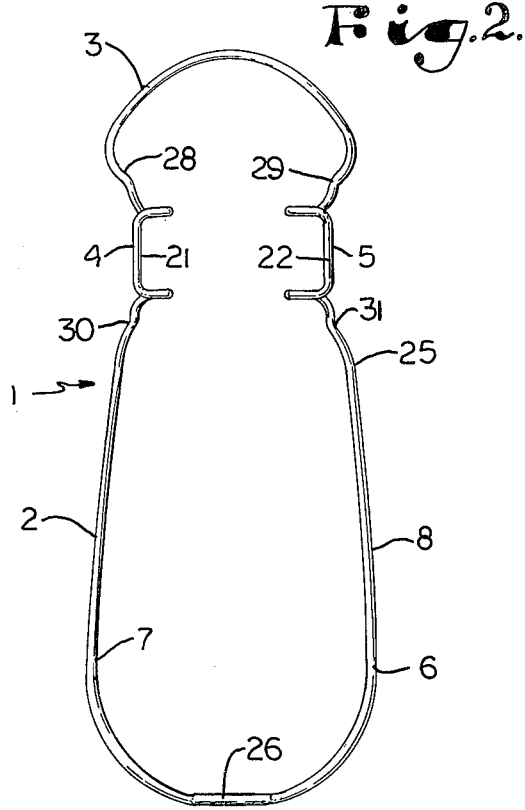
Fig. 2.
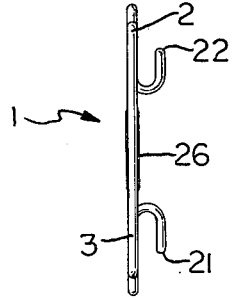
Fig. 3.
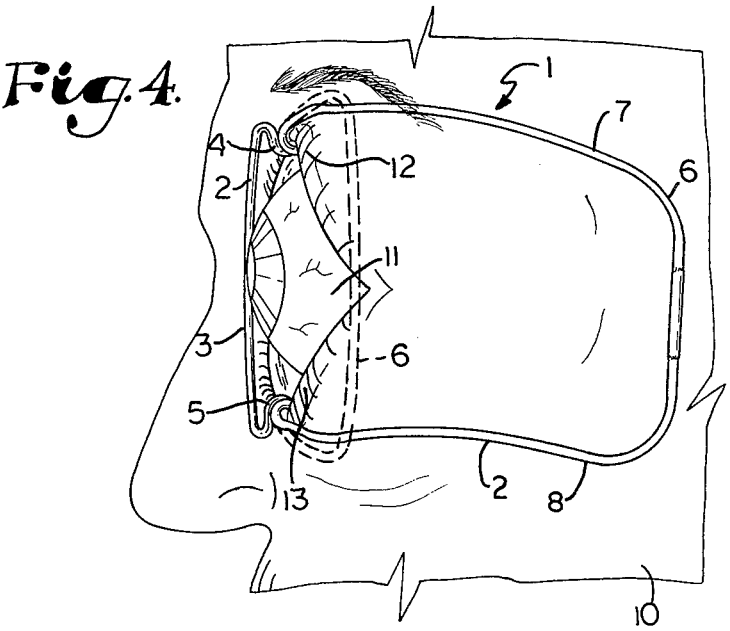
Fig. 4.
Fig. 5.

EYELID RETRACTOR

BACKGROUND OF THE INVENTION

The present invention relates to specula, and in particular to specula of the eyelid retractor type for use in ocular surgery or the like wherein the eyelids must be drawn back or open to allow access to the eyeball.

Conventional eyelid retractors are typically characterized by screw locking devices, knobs, and/or pointed ends. These screw locking devices, knobs, and pointed ends tend to snag or catch suturing material normally used in eye surgery. Such suturing material is very fine and is thus often broken or caught increasing the time and labor of such surgery. Even if the suturing material is not caught, sharp and/or pointed portions of such eye retractors present a constant threat of suture breakage which in turn slows surgery as doctors must be extra careful to avoid such breakage.

The conventional eyelid retractors often utilize spring mechanisms to bias apart the eyelids. Such spring mechanisms often tend to produce a post-operative effect known as ptosis or drooping of the eyelid. Ptosis is normally the result of excessive pressure being placed on the eyelid muscles by the eyelid retractor, especially a spring portion thereof, during surgery. Conventional spring mechanisms are believed to cause the ptosis sincce they are often uncontrolled or when controlled by a locking device, there is normally some difficulty in properly adjusting the associated locking device to apply just the proper separative pressure.

In addition many conventional eyelid retractors are not self supporting. Such retractors often extend horizontally from the eye and thus require some support to sustain such a horizontal attitude. Even those retractors which are preformed to somewhat follow the contour of the face, are not adjustable for variances in face structure and therefore often transmit a torque to the eyelids, which torque is also believed to cause ptosis.

During ocular surgery or the like, it is often necessary to utilize extensive equipment which must be placed relatively close to the eye and/or face area surrounding the eye. Typical of such equipment is the Kelman Phaco Emulsification Unit used in cataract removal. As conventional eye retractors often have portions extending above the face area surrounding the eye, a surgeon must either use alternative and sometimes less desirable equipment or remove the eyelid retractor such that the eyelids are then in the operative way of the surgeon.

Conventional eyelid retractors are typically only slightly, if at all, adjustable to the face and/or eye of the patient. Such retractors infrequently come in varying sizes. The most standard adjustment is in control of the spread or distance between the eyelids, which distance is normally produced by the urging of a hairpin, coil, or the like type of spring. The age, sex, race, and general facial structure, especially the bone structure, of each patient present substantially different features to a surgeon in every operation, which features can not generally be conformed to by conventional eyelid retractors. Preferably a different eyelid retractor should be utilized for each patient which retractor conforms to the particular feature of that patient.

In addition conventional eyelid retractors often have moving parts, must be manufactured to fine tolerances and must be constructed so as to retain such tolerances, all of which tend to increase the cost of such retractors. Thus, it is desirable to produce a retractor which is relatively inexpensive compared to conventional retractors and thereby reduce operating expense.

OBJECTS OF THE INVENTION

Therefore the objects of the present invention are: to provide a speculum especially suited as an eyelid retractor; to provide such a speculum which is a smooth loop characterized by lack of knobs, screws, or pointed features upon which a suture may snag or break; to provide such a speculum which is also characterized by absence of a biasing spring but rather is characterized by malleability of the speculum which allows adjustment thereof to conform to the eyelids to be separated such that, in conjunction with sufficient stiffness or resiliency associated therewith, the speculum maintains the eyelids in a precise position determined by the operating physician; to provide such a speculum which is self supporting and, in particular, is sufficiently malleable to conform to the features of the face and be supported thereby; to provide such a speculum which has a low profile in the area surrounding the eye such that various equipment may be used during an operative procedure without interference therefrom; to provide such a speculum which conforms to the facial features of each individual patient; to provide such a speculum which reduces ocular operating time; to provide such a speculum which is relatively inexpensive to produce; and to provide such a speculum which is easy to manufacture, simple to use, and which is particularly well adapted for the proposed usage thereof.

Other objects and advantages of this invention will become apparent from the following description taken in connection with the accompanying drawings wherein are set forth by way of illustration and example, certain embodiments of this invention.

SUMMARY OF THE INVENTION

An eyelid retractor is provided for biasing eyelids away from a covering position over an eye upon which ocular surgery or a similar process is being performed. The retractor comprises a continuous loop having no sharp or pointed edges upon which suture thread may snag or break. Preferably blades or eyelid engaging portions on the retractor are intergrated into the loop.

The retractor is also malleable to the extent that a surgeon may shape by hand the retractor prior to application thereof to a patient such that the blades are positioned to provide proper separation of the eyelids without placing excessive ptosis causing pressure thereon. The retractor is also sufficiently stiff or resilient to substantially maintain the shape into which same is positioned by the surgeon against the eyelids. In addition, the retractor has a handle portion which is also malleable such that the handle may be shaped to conform to the facial features of a patient. The handle along with the remainder of the retractor in this manner rests on and is supported by the face of the patient. Also, in this manner the retractor does not require additional support or tend to sag during an operation which sagging would tend to create ptosis causing torque on the eyelids. The retractor except for the portion of the blades beneath the eyelids is face hugging thereby exhibiting a low profile such that various equipment may be utilized in close proximity to the eye and area surrounding the eye without removing the retractor.

Once in position on the patient, the retractor of the present invention need not be removed until the operation is completed. As there are no suture snagging portions of the retractor, the surgeon can suture with less concern over such snagging and thereby substantially reduce operating time.

The drawings constitute a part of this specification and include exemplary embodiments of the present invention and illustrate various objects and features thereof.

BRIEF DESCRIPTION OF THE DRAWINGS

FIG. 1 is a perspective view of an eyelid retractor according to the present invention.

FIG. 2 is a bottom plan view of the eyelid retractor.

FIG. 3 is an end view of the eyelid retractor.

FIG. 4 is a slightly enlarged perspective view of the eyelid retractor in eyelid retracting position on the face of a patient showing a pre-use shape thereof in phantom.

FIG. 5 is a side elevational view of the eyelid retractor.

DETAILED DESCRIPTION OF THE PREFERRED EMBODIMENT

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 generally designates a speculum or eyelid retractor according to the present invention.

The retractor 1 comprises a circuitous structural member or loop 2 having a relatively smooth surface and having a nose or bridge portion 3, a pair of blade portions 4 and 5 and handle portion 6. The bridge portion 3 is generally arcuate and interconnects one end of each of the blade portions 4 and 5. The handle portion 6 is generally arcuate or U-shaped and interconnects a second end of the blade portions 4 and 5. The handle portion 6 has legs or sides 7 and 8.

The illustrated retractor 1 has a pre-use configuration as shown in FIGS. 1, 2, 3 and 5 wherein the bridge portion 3 and handle portion 6 are substantially planar. The retractor 1 also has an eyelid retracting configuration, as shown in FIG. 4, wherein the retractor 1 is formed or bent to conform to the face 10 of the patient and, in particular, the handle portion 6 is bent to rest on or hug the surface of the face 10 of the patient laterally or toward the ear on the same side of the face 10 associated with an eye 11 and pair of eyelids 12 and 13 which are subject to surgery or other operation requiring that the eyelids 12 and 13 be in a non-covering position, as seen in FIG. 4, relative to the eye 11.

The blade portions 4 and 5 comprise an eyelid edge engaging and restraining means or members, such as illustrated blades 15 and 16 respectively, depending from the loop 2. Each blade 15 and 16 is attached to the loop 2 at one end 17 and 18 respectively thereof. From the ends 17 and 18 the blades 15 and 16 respectively bend toward one another, then circle back in opposed relationship to one another to second ends 21 and 22 respectively thereof. Each of the blades 15 and 16 thus form or define a U- or V-shaped notch or cradle which engages one edge of an associated eyelid 12 and 13 respectively in opposed fashion when the retractor 1 is in the eyelid retracting configuration.

Preferably the blades 15 and 16 are integrated within the loop 2 such that the retractor 1 is formed from one generally endless strip or wire. The illustrated loop 2 is a single wire 25 joined at a center of the handle portion 6 by a sleeve or connector member 26. The loop also includes slight indentations or juts 28 and 29 on the side of each blade 15 and 16 respectively associated with the bridge portion 3 and similiar indentations or juts 30 and 31 on the side of each blade 15 and 16 respectively associated with the handle portion 6. The juts 28, 29, 30 and 31 facilitate bending or manipulation of the retractor in the horizontal plane associated with the pre-use configuration thereof.

The retractor is preferably constructed of material which is sufficiently malleable so as to allow a surgeon or other person adjusting the retractor 1 to manually bend or inelastically deform the retractor 1 with relative ease into a desired shape to conform to particular features of a patient. In particular, the blade portions 4 and 5 are malleable so as to allow the blades 15 and 16 to be spaced and/or rotated relative to one another so as to provide optimum position of the eyelids of the particular patient during surgery. Also the bridge portion 3 and handle portion 6 are suitably malleable such that the retractor may be bent to rest on or hug the face 10 of the patient and present a low profile relative thereto. The retractor 1 also is characterized by being sufficiently stiff or resilient so as to substantially maintain the shape thereof when formed into the eyelid retracting configuration, especially as related to pressure exerted thereon by the eyelids 12 and 13 when the eyelids are attempting to close. This resiliency is preferably naturally inherent in the material of construction of the retractor 1 and not induced by a spring or the like. While it is foreseen that many materials compatible with surgery requirements would fit such malleable yet resilient characteristics, it has been found that 302 stainless steel wire of 0.045 inch diameter and having a tensile rating of between 80,000 and 120,000 pounds per square inch will work very satisfactorily for this purpose.

In use a surgeon or other suitable party normally first sterilizes the retractor in the pre-use configuration of FIG. 1. When necessary the blades 15 and 16 are rotated relative to each other to conform to the desired angle of engagement with the eyelids 12 and 13 respectively. The handle portion sides 7 and 8 are then pinched or urged toward one another by applying pressure thereto from the thumb and forefinger until blade ends 21 and 22 will slip or pass under the eyelids 12 and 13 respectively associated therewith.

The pressure is then reversed on the handle portion sides 7 and 8 until the eyelids 12 and 13 are satisfactorily spaced or separated such that the eye 11 is not covered thereby and such that the eyelids 12 and 13 are not unnecessarily biased apart so as to cause ptosis. Pressure is released from the sides 7 and 8 which substantially retain the position thereof when released. The retractor 1 is then held in both hands as the bridge portion 5 and handle portion 6 are urged or bent to conform to and rest on the structure of the face 10, thereby tending to support and stabilize the retractor 1. The modulus of elasticity of the retractor 1 is such that the surgeon's manual pressure inelastically deformed same but the lesser pressure exerted by the eyelids 12 and 13 is unable to substantially deform same, thus the eyelids 12 and 13 are retained in desired operating positions thereof.

Upon completion of the operation, the sides 7 and 8 are again urged together until the blades 15 and 16 are free to readily slide past the eyelids 12 and 13 respectively after which the retractor 1 is raised from the face 10. The retractor 1 may be reshaped and reused or discarded according to the preference of the user.

It is noted that while the present invention has been described in use as an eyelid retractor, such a retractor could be equivalently utilized for other similar medical purposes.

It is to be understood that while certain embodiments of the present invention have been illustrated and described, it is not to be limited to the specific forms or arrangement of parts herein described and shown.

What is claimed and desired to secure by Letters Patent is as follows:

1. A speculum adapted for use in retracting eyelids during ocular operations comprising:
   (a) a closed and one-piece loop; said loop being inelastically deformable by digital pressure exerted thereon by a doctor to a desired shape so as to conform to facial features of a patient and thereafter hold said shape against pressure exerted thereon by the eyelids; and
   (b) a pair of blades opposingly positioned and connected with said loop; said blades being adapted for engaging the eyelids; said speculum having an eyelid retracting configuration wherein said loop is positioned relative to an eye such that eyelids associated with the eye are held apart by the blades.

2. The speculum according to claim 1 wherein:
   (a) said loop is a smooth surfaced wire; said wire being free of sharp and pointed edges.

3. The speculum according to claim 2 wherein:
   (a) said blades are an integrated portion of said loop; said wire is continuous and endless and is twisted so as to define said loop and said blades.

4. The speculum according to claim 1, 2 or 3 wherein:
   (a) said loop contains a handle portion; and
   (b) said handle is manually malleable such that when said speculum is in said eyelid retracting configuration, said handle portion is inelastically bent to conform to surface features on the face of the patient whereby said speculum is face hugging and is supported by a portion of the face surrounding the eye of the patient.

5. The speculum according to claim 1, 2 or 3 wherein:
   (a) said loop is constructed from about 0.045 inch diameter stainless steel wire.

6. The speculum according to claim 5 wherein:
   (a) said wire is 302 stainless steel having a tensile rating between 80,000 and 120,000 pounds per square inch.

7. An eyelid retractor comprising:
   (a) one piece stainless steel structural member having a non-use configuration;
   (b) a pair of eyelid restraining blades interconnected by said structural member;
   (c) said structural member being sufficiently malleable substantially along the entire length thereof by digital pressure of a user to be inelastically deformed so as to maintain a use configuration normally different from said non-use configuration for positioning eyelids during ocular surgery; said structural member being also sufficiently stiff to be substantially non-deformed by pressure applied by eyelids thereto, whereby said blades may be manually positioned to retain the eyelids in a selected position.

8. The retractor according to claim 7 wherein:
   (a) said structural member includes a handle portion connecting said blades; and wherein
   (b) said handle portion is sufficiently malleable to be manually non-elastically deformed to conform to facial features of a patient utilizing said retractor; whereby said retractor rests on and is supported by the face of the patient when said retractor is in an eyelid retracting configuration.

9. The retractor according to claim 8 wherein:
   (a) said handle portion connects first ends of said blades and said blades have second ends; and wherein
   (b) said structural member includes a bridge portion connecting the second ends of said blades; and
   (c) said bridge portion is malleable so as to be manually conformable to the face of the patient.

10. The retractor according to claims 7, 8 or 9 wherein:
    (a) said structural member is about 0.045 inch diameter 302 stainless steel having a tensile range of about 80,000 to 120,000 pounds square inch.

11. A speculum adapted for use in retracting eyelids during ocular operations comprising:
    (a) a closed loop structure formed by a single piece of continuous wire including a bridge portion and a handle portion;
    (b) a pair of blades opposingly positioned and connected with said loop structure; each blade being between said bridge and handle portions; said blades being adapted for engaging the eyelids; said speculum having an eyelid retracting configuration wherein said loop structure is positioned relative to an eye such that eyelids associated with the eye are held apart by the blades; and wherein:
    (c) said bridge and handle portions are inelastically deformable therealong by digital pressure exerted thereon to conform to the facial features of a patient.

12. A speculum adapted for use in retracting eyelids comprising:
    (a) a loop structure having a pair of opposing blades attached thereto; said loop structure being inelastically deformable along the entire length thereof by digital pressure exerted by a user such that said loop structure may be selectively modified from a non-eyelid retracting configuration to an eyelid retracting configuration wherein said blades are adapted to hold eyelids in a selected retracted position and such that said loop structure is conformable to the facial feature of a patient whereby said speculum presents a low profile on the patient when in said eyelid retracting configuration.

13. The speculum according to claim 12 wherein:
    (a) said loop structure is one-piece and includes a bridge portion connecting said blades on the nose side of an eye of a patient and a handle portion for connecting said blades on the side of the eye opposite the nose side.

14. A speculum adapted for use in retracting eyelids comprising:
    (a) a loop structure comprising in sequence:
        (1) a handle portion;
        (2) a first eyelid restraining blade;
        (3) a bridge portion; and
        (4) a second eyelid restraining blade; and (b) a plurality of malleable juts; each of said juts hingedly connecting one of said blades to one of said portions; such that the position of said blades may be modified relative to one another without modifying the position of said bridge portion relative to said handle portion and the position of said bridge portion may be modified relative to said handle portion without modifying the position of said first blade relative to said second blade.

15. The speculum according to claim 14 wherein:
(a) said speculum is of one-piece construction and selectively inelastically deformable entirely therealong by digital pressure of a user to conform to a face of a patient when in an eyelid retracting position thereof and to restrain eyelids of the patient from closing when in such position.

* * * * *